(12) United States Patent
Takemura et al.

(10) Patent No.: US 8,284,245 B2
(45) Date of Patent: Oct. 9, 2012

(54) IMAGE PROCESSING APPARATUS, ENDOSCOPE APPARATUS AND COLOR BALANCE ADJUSTING METHOD

(75) Inventors: Takashi Takemura, Tokyo (JP); Takeshi Urasaki, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 1361 days.

(21) Appl. No.: 11/914,508

(22) PCT Filed: Mar. 1, 2006

(86) PCT No.: PCT/JP2006/303880
§ 371 (c)(1),
(2), (4) Date: Nov. 15, 2007

(87) PCT Pub. No.: WO2006/126318
PCT Pub. Date: Nov. 30, 2006

(65) Prior Publication Data
US 2009/0073261 A1    Mar. 19, 2009

(30) Foreign Application Priority Data
May 23, 2005   (JP) .................................. 2005-149886

(51) Int. Cl.
*A61B 1/04*   (2006.01)
(52) U.S. Cl. .......................................... 348/71; 348/65
(58) Field of Classification Search .................... 348/65, 348/71
See application file for complete search history.

(56) References Cited

U.S. PATENT DOCUMENTS

| 4,870,454 | A | * | 9/1989 | Kurusu et al. .................. 355/69 |
| 5,007,408 | A | * | 4/1991 | Ieoka ........................... 600/109 |
| 5,504,524 | A | | 4/1996 | Lu et al. |
| 5,867,284 | A | * | 2/1999 | Heinrichs et al. ............. 358/516 |
| 6,151,064 | A | | 11/2000 | Connolly et al. |

(Continued)

FOREIGN PATENT DOCUMENTS
EP   1 488 732 A1   12/2004
(Continued)

OTHER PUBLICATIONS

Extended Supplementary European Search Report dated Nov. 18, 2009.

(Continued)

*Primary Examiner* — Firmin Backer
*Assistant Examiner* — Jonathan Bui
(74) *Attorney, Agent, or Firm* — Scully, Scott, Murphy & Presser, P.C.

(57) ABSTRACT

There are provided an image processing apparatus, an endoscope apparatus, and a color balance adjusting method capable of obtaining a good observation image. An image processing apparatus of the invention includes: an image signal input unit for inputting an image signal of a subject image picked up by an image pickup unit, the subject image including at least an image of a color balance adjustment tool; a control unit for calculating a value of coefficient to change brightness value of the image signal, based on a correction value to correct characteristic variation of the color balance adjustment tool, the correction value being shown in a correction value display portion included by the color balance adjustment tool, and a brightness value of the image of the color balance adjustment tool; and a color balance process unit for performing color balance adjustment by changing the brightness value of the image signal based on the coefficient value.

12 Claims, 11 Drawing Sheets

U.S. PATENT DOCUMENTS

| | | |
|---|---|---|
| 6,206,825 B1 * | 3/2001 | Tsuyuki .................. 600/182 |
| 6,268,940 B1 | 7/2001 | Saarelma et al. |
| 6,293,911 B1 | 9/2001 | Imaizumi et al. |
| 6,307,638 B1 | 10/2001 | Matsumoto |
| 6,650,365 B1 | 11/2003 | Sato |
| 6,717,609 B2 | 4/2004 | Sugimoto et al. |
| 6,876,399 B1 | 4/2005 | Masuyama et al. |
| 6,937,269 B2 | 8/2005 | Sugimoto et al. |
| 2002/0013512 A1 * | 1/2002 | Sendai et al. ............ 600/160 |
| 2002/0014595 A1 * | 2/2002 | Sendai et al. ............ 250/458.1 |
| 2002/0080246 A1 | 6/2002 | Parulski |
| 2002/0188173 A1 | 12/2002 | Kobayashi |
| 2003/0001951 A1 * | 1/2003 | Tsujita et al. ............ 348/65 |
| 2004/0215060 A1 * | 10/2004 | Ueno et al. ............ 600/160 |
| 2004/0267091 A1 | 12/2004 | Imaizumi et al. |
| 2005/0014996 A1 * | 1/2005 | Konomura et al. ........ 600/175 |
| 2005/0078175 A1 * | 4/2005 | Kaneko ..................... 348/65 |
| 2005/0203423 A1 * | 9/2005 | Zeng et al. ............... 600/476 |
| 2005/0237416 A1 * | 10/2005 | Hasegawa ............... 348/335 |
| 2007/0203413 A1 * | 8/2007 | Frangioni ............... 600/478 |

FOREIGN PATENT DOCUMENTS

| | | |
|---|---|---|
| EP | 1 527 729 A1 | 5/2005 |
| JP | 04-069615 | 3/1992 |
| JP | 04069615 A * | 3/1992 |
| JP | 10-201707 | 8/1998 |
| JP | 11-089789 | 4/1999 |
| JP | 2002-336196 A | 11/2002 |
| JP | 2003-265410 | 9/2003 |
| JP | 2005-033282 | 2/2005 |

OTHER PUBLICATIONS

Official Action dated Oct. 19, 2009 received from the Australian Patent Office.
US 6,692,429, 02/2004, Imaizumi et al. (withdrawn)

* cited by examiner

FIG.5
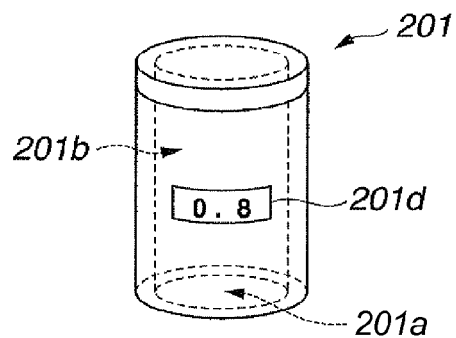
FIG.6
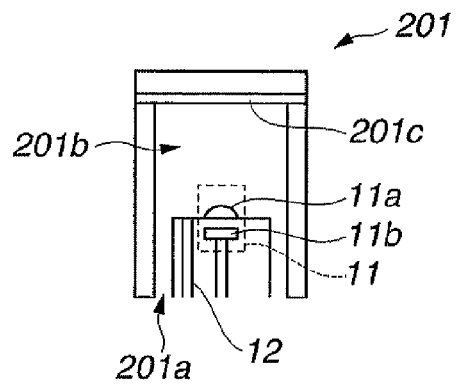
FIG.7
PLEASE PREPARE AFI COLOR BALANCE CAP
PLEASE INPUT CAP CORRECTION VALUE
AFI CAP CORRECTION VALUE
───301
← → CHANGE SETTING
"ENTER" SAVE & END     "ESC" END     "SETTING" END    ～301A

IMAGE PROCESSING APPARATUS, ENDOSCOPE APPARATUS AND COLOR BALANCE ADJUSTING METHOD

TECHNICAL FIELD

The present invention relates to an image processing apparatus, an endoscope apparatus, and a color balance adjusting method, and in particular, to an image processing apparatus, an endoscope apparatus, and a color balance adjusting method capable of correcting characteristic variation that occurs with a color balance adjustment tool when performing color balance adjustments.

BACKGROUND ART

Endoscope apparatuses having an endoscope, a light source apparatus, and so on have conventionally been widely used in the medical field and the like. In particular, endoscope apparatuses used in the medical field are mainly used for the purpose of allowing a user to perform treatments such as inspection and observation of the inside of a living body. Generally known observations using the endoscope apparatus in the medical field include, for example, normal observation, in which white light is irradiated into a living body to pick up an image of the inside of the living body which is generally the same as in naked-eye observation, and additionally thereto, fluorescent light observation, in which excitation light including a specific wavelength band is irradiated into a living body to pick up an image of auto-fluorescent light emitted by biological tissues in the living body, the auto-fluorescent light image being observed to determine a normal region and a lesion region in the living body.

In general, when performing a treatment such as inspection and observation with an endoscope, white balance adjustments respectively supporting observation modes of the endoscope apparatus are performed before the observation in order to adjust variation in color reproduction due to variations such as in sensitivity of a solid-state image pickup device in the endoscope, in optical characteristics of filter, lens or the like of a light source apparatus, and in chromatic aberration when the endoscope and the light source apparatus are connected to each other. For example, even in the case of performing treatments such as inspection and observation using endoscope apparatuses that are proposed in Japanese unexamined patent publications Nos. 11-089789 and 10-201707, before each observation, there are performed white balance adjustment as one of color balance adjustments, which is performed by picking up an image of a subject for normal observation, and color balance adjustment which is performed by picking up an image of a subject for fluorescent light observation.

The subjects used for the color balance adjustments including the above-mentioned white balance adjustment include, for example, one having a fluorescent member as a fluorescent light generating portion that emits fluorescent light by light. Of the above-mentioned subjects used for the color balance adjustments including the white balance adjustment, especially those having the fluorescent member are easily subjected to characteristic variations that occur in manufacture, such as, for example, variation in intensity of fluorescent light emitted by the fluorescent member.

It is desirable that the color balance adjustments supporting the observation modes of the endoscope apparatus, which are performed before each observation with the endoscope apparatus, are performed taking into consideration characteristic variation of the subject used for the color balance adjustment, in addition to the above-mentioned characteristic variation at each part of the endoscope apparatus.

However, in a fluorescent imaging apparatus of Japanese unexamined patent publication No. 11-089789 and an endoscope apparatus of Japanese unexamined patent publication No. 10-201707, no consideration is taken for characteristic variation of the subject that is used for white balance adjustment being performed, resulting in a problem that it is difficult to obtain a good observation image.

The present invention has been made in view of the above, and an object of the present invention is to provide an image processing apparatus, an endoscope apparatus, and a color balance adjusting method capable of obtaining a good observation image.

DISCLOSURE OF INVENTION

Means for Solving the Problem

An image processing apparatus of a first aspect of the present invention includes: an image signal input unit for inputting an image signal of a subject image picked up by an image pickup unit, the subject image including at least an image of a color balance adjustment tool; a control unit for calculating a value of coefficient to change brightness value of the image signal, based on a correction value to correct characteristic variation of the color balance adjustment tool, the correction value being shown in a correction value display portion included by the color balance adjustment tool, and a brightness value of the image of the color balance adjustment tool; and a color balance process unit for performing color balance adjustment by changing the brightness value of the image signal based on the coefficient value.

An image processing apparatus of a second aspect of the present invention is the image processing apparatus of the first aspect, wherein the color balance adjustment tool has a tubular body provided with an aperture portion with a diameter to allow insertion of a distal end portion of an endoscope.

An image processing apparatus of a third aspect of the present invention is the image processing apparatus of the first aspect, wherein the color balance adjustment tool includes a fluorescent light generating portion to emit fluorescent light, the fluorescent light generating portion being provided to be included in at least a part of the image of the color balance adjustment tool picked up by the image pickup unit.

An image processing apparatus of a fourth aspect of the present invention is the image processing apparatus of the third aspect, wherein the characteristic variation is variation in intensity of the fluorescent light.

An image processing apparatus of a fifth aspect of the present invention is the image processing apparatus of the first aspect, wherein the control unit performs control to cause a display apparatus to display a correction value input screen including a correction value input portion for inputting the correction value.

An image processing apparatus of a sixth aspect of the present invention is the image processing apparatus of the fifth aspect, wherein the correction value input screen is a screen that is displayed including an operation guiding portion for showing a list of operations executable on the correction value input screen, and a message to urge a user to prepare necessary operations in inputting the correction value into the correction value input portion.

An endoscope apparatus of a first aspect of the present invention includes: an endoscope including an image pickup unit for picking up a subject image including at least an image of a color balance adjustment tool and outputting the picked-up image as an image signal; and an image processing apparatus for performing color balance adjustment on the image signal, wherein the image processing apparatus calculates a value of coefficient to be used for the color balance adjustment, based on a brightness value of an image of the color balance adjustment tool picked up by the image pickup unit, and a correction value based on characteristic variation occurring with the color balance adjustment tool.

An endoscope apparatus of a second aspect of the present invention is the endoscope apparatus of the first aspect, wherein the color balance adjustment tool has a tubular body provided with an aperture portion with a diameter to allow insertion of a distal end portion of the endoscope.

An endoscope apparatus of a third aspect of the present invention is the endoscope apparatus of the first aspect, wherein the color balance adjustment tool includes a fluorescent light generating portion to emit fluorescent light, the fluorescent light generating portion being provided to be included in at least a part of the image of the color balance adjustment tool picked up by the image pickup unit.

An endoscope apparatus of a fourth aspect of the present invention is the endoscope apparatus of the third aspect, wherein the characteristic variation is a variation in intensity of the fluorescent light.

An endoscope apparatus of a fifth aspect of the present invention is the endoscope apparatus of the first aspect, wherein the control unit performs control to cause a display apparatus to display a correction value input screen including a correction value input portion for inputting the correction value.

An endoscope apparatus of a sixth aspect of the present invention is the endoscope apparatus of the fifth aspect, wherein the correction value input screen is a screen that is displayed including an operation guiding portion for showing a list of operations executable on the correction value input screen, and a message to urge a user to prepare necessary operations in inputting the correction value into the correction value input portion.

A color balance adjusting method of a first aspect of the present invention includes: an image signal input step for inputting an image signal of a subject image picked up by an image pickup unit, the subject image including at least an image of a color balance adjustment tool; a correction value input judgment step for judging whether or not there has been input of a correction value for correcting characteristic variation of the color balance adjustment tool, the correction value being shown in a correction value display portion included by the color balance adjustment tool; a brightness value calculation step for calculating, based on the image signal, a mean value of brightness values in an image including one wavelength band and a mean value of brightness values in an image including another wavelength band; and a coefficient calculation step for calculating a value of coefficient to be used for color balance adjustment, based on the correction value and each of the mean values calculated in the brightness value calculation step.

A color balance adjusting method of a second aspect of the present invention is the color balance adjusting method of the first aspect, wherein the color balance adjustment tool includes a fluorescent light generating portion to emit fluorescent light, the fluorescent light generating portion being provided to be included in at least a part of the image of the color balance adjustment tool picked up by the image pickup unit.

A color balance adjusting method of a third aspect of the present invention is the color balance adjusting method of the first aspect, wherein the characteristic variation is variation in intensity of the fluorescent light.

BRIEF DESCRIPTION OF THE DRAWINGS

FIG. 5 is a view showing an appearance of an endoscope color-balance-adjustment tool used for the endoscope apparatus of the present embodiment.

FIG. 6 is a section view of the endoscope color-balance-adjustment tool shown in FIG. 5.

FIG. 7 is a view showing an exemplary correction value input screen displayed on a monitor by the image processing apparatus of the present embodiment.

BEST MODE FOR CARRYING OUT THE INVENTION

Figure 1:
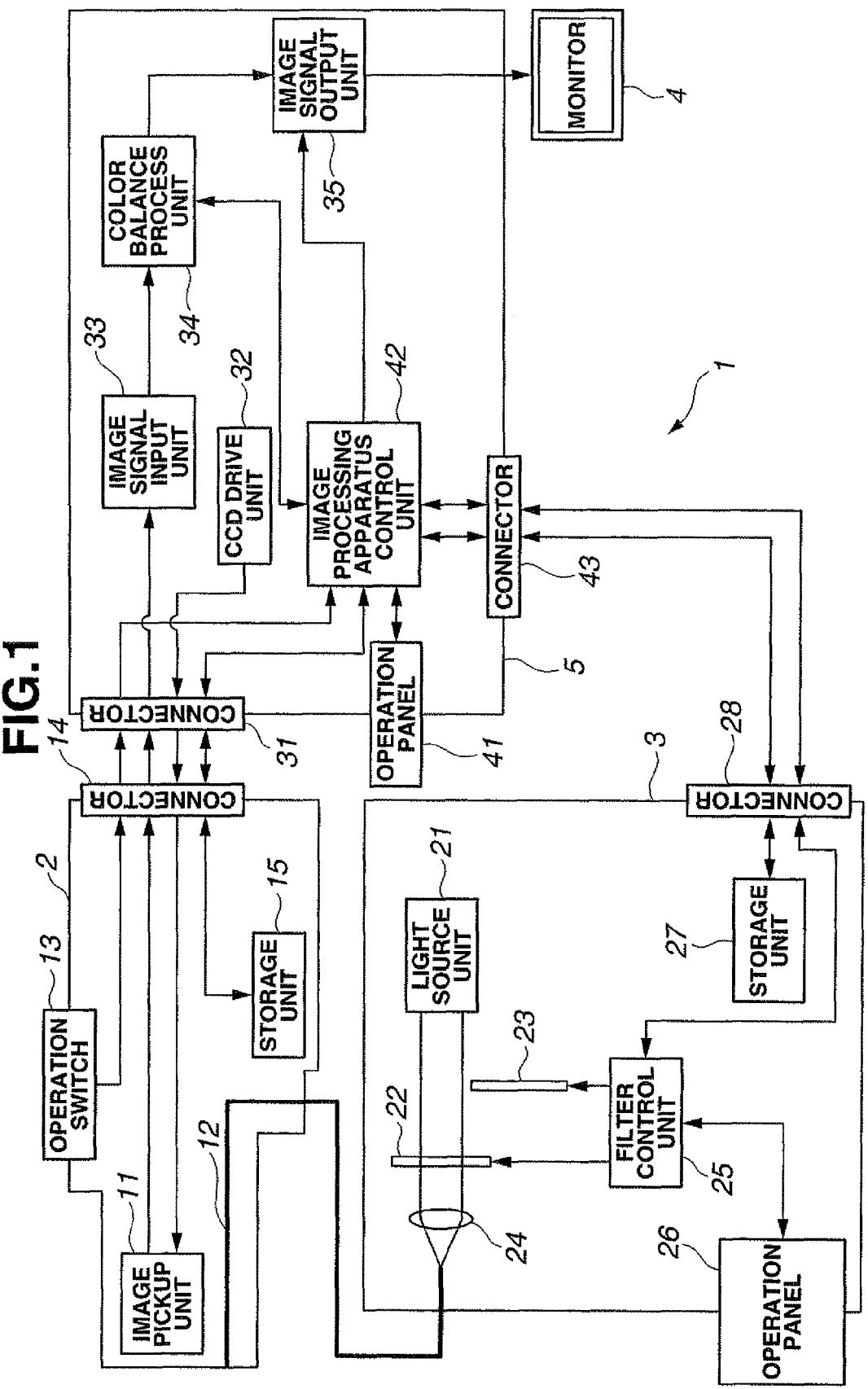
FIG. 1 is a block diagram showing an exemplary configuration of an endoscope apparatus of the present embodiment.
Figure 2:
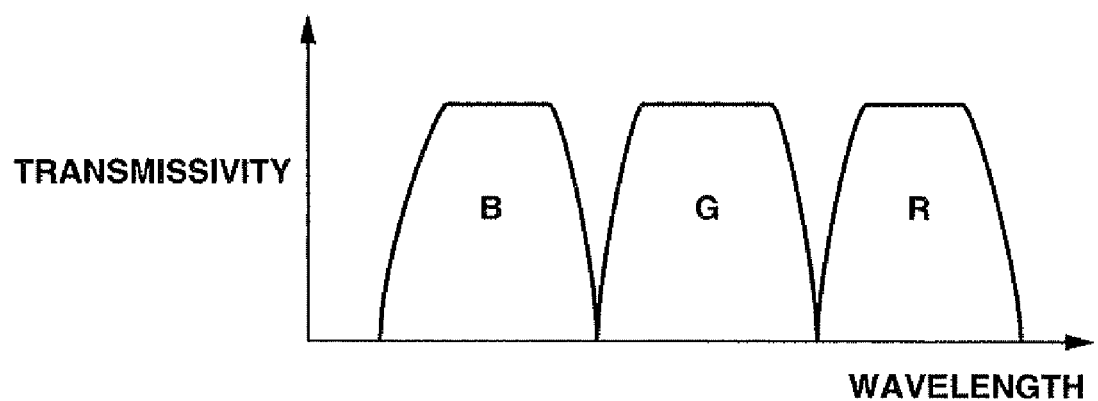
FIG. 2 is a view showing correlation between bands and transmissivities of an RGB filter included by a light source apparatus of the endoscope apparatus of the present embodiment.
Figure 3:
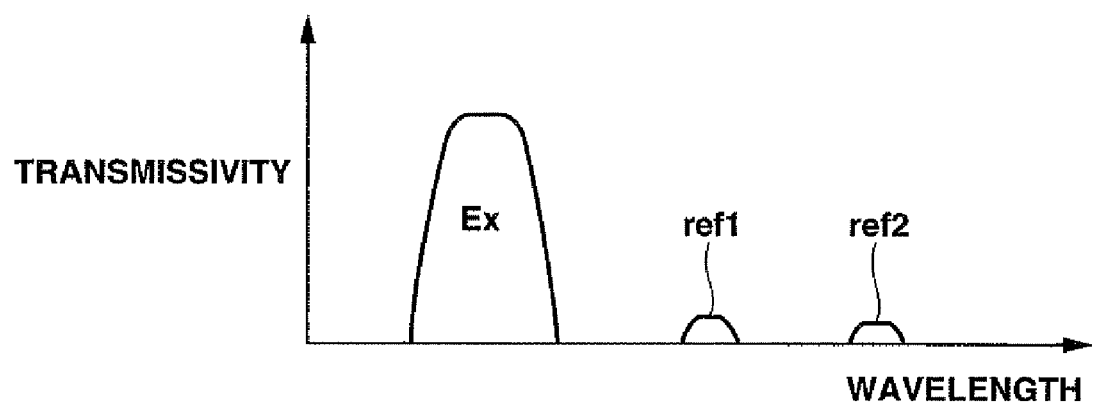
FIG. 3 is a view showing correlation between bands and transmissivities of a fluorescent light observation filter included by the light source apparatus of the endoscope apparatus of the present embodiment.
Figure 4:
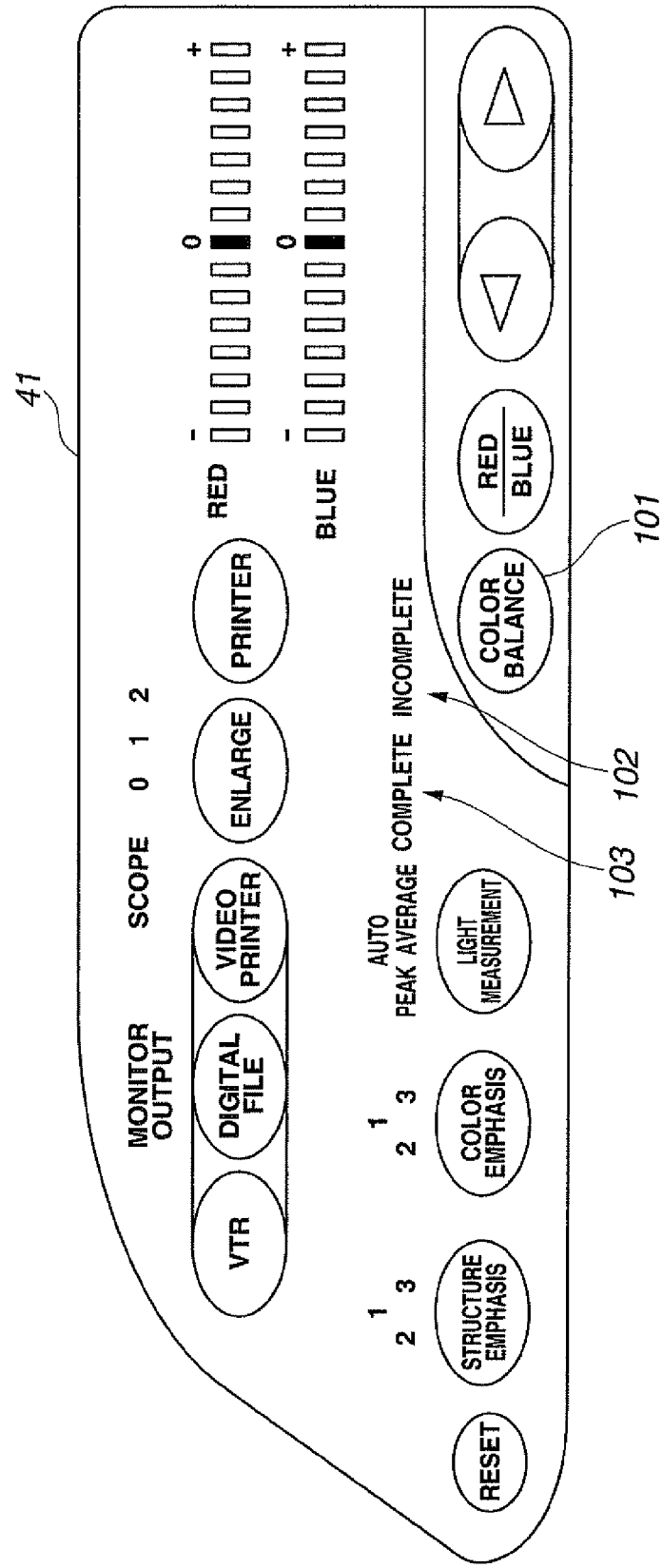
FIG. 4 is a view showing an operation panel provided to an image processing apparatus configuring the endoscope apparatus of the present embodiment.
Figure 8:
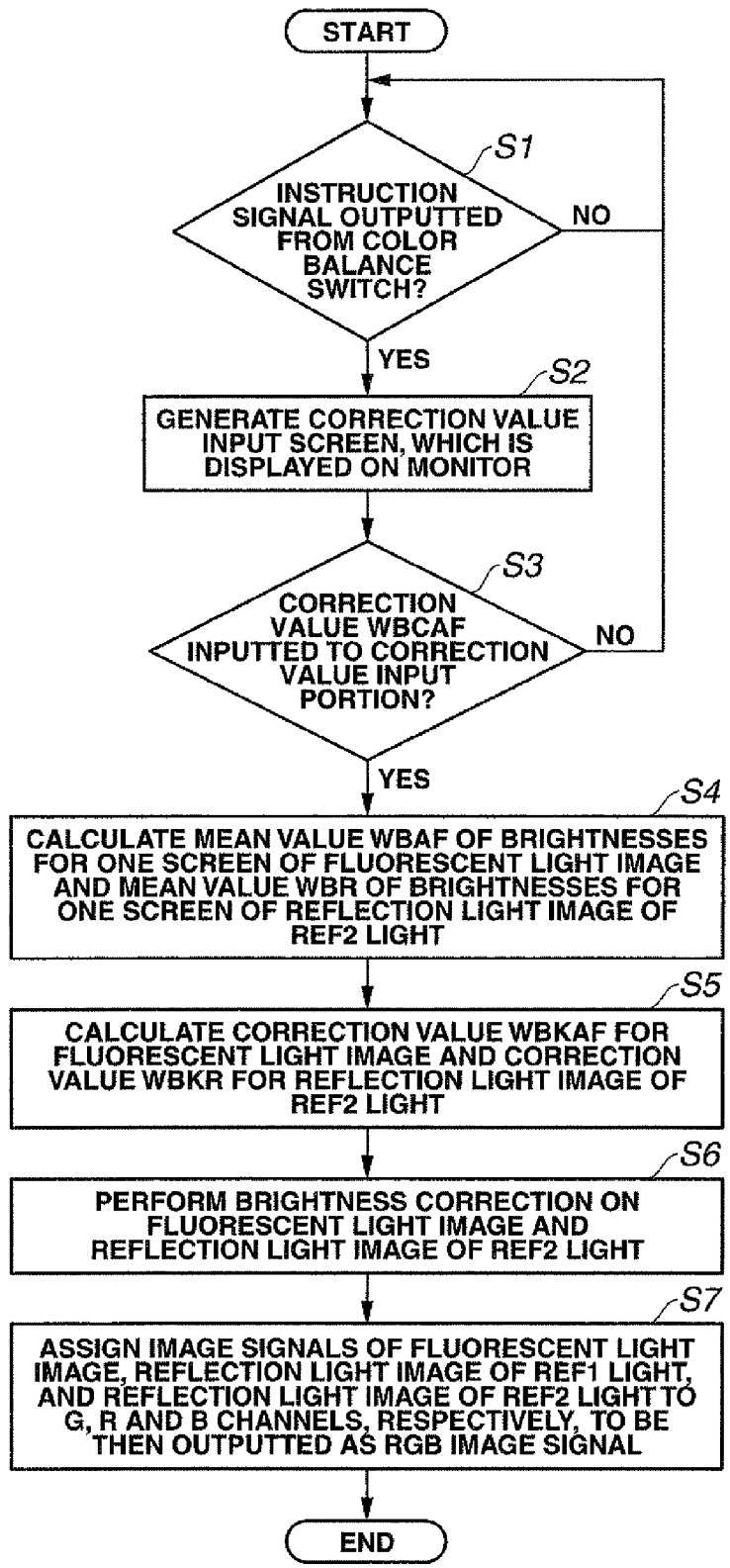
FIG. 8 is a flow chart showing an exemplary processing to be performed in color balance adjustment by the image processing apparatus of the present embodiment.
Figure 9:
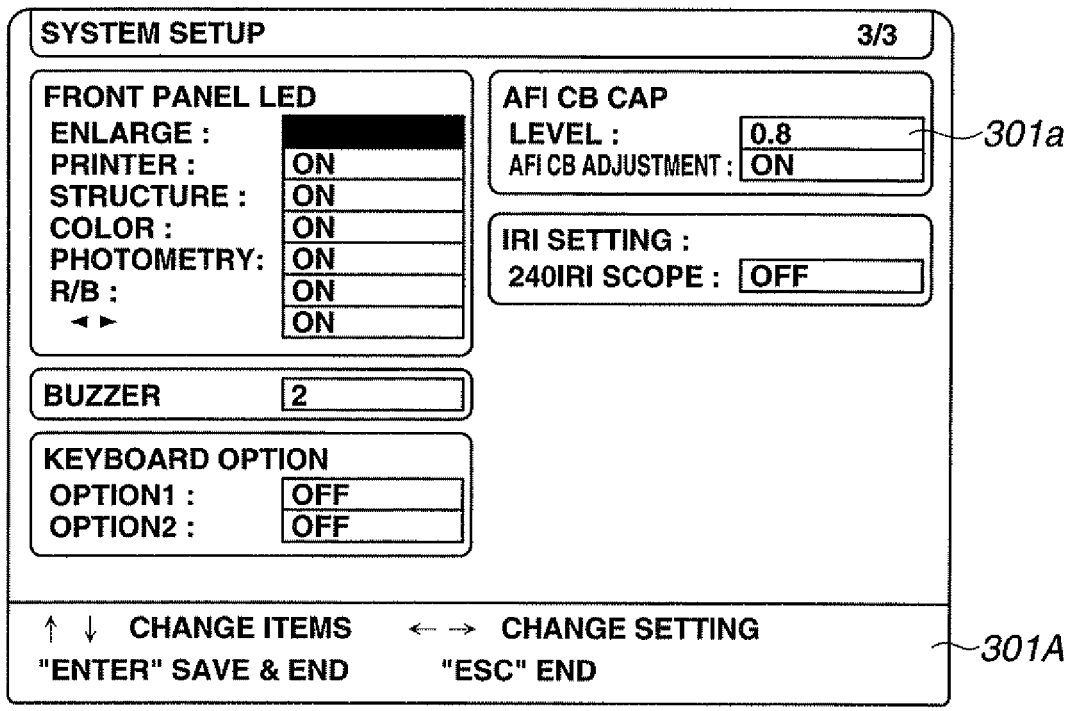
FIG. 9 is a view showing an exemplary menu screen displayed on the monitor, in the endoscope apparatus of the present embodiment.
Figure 10:
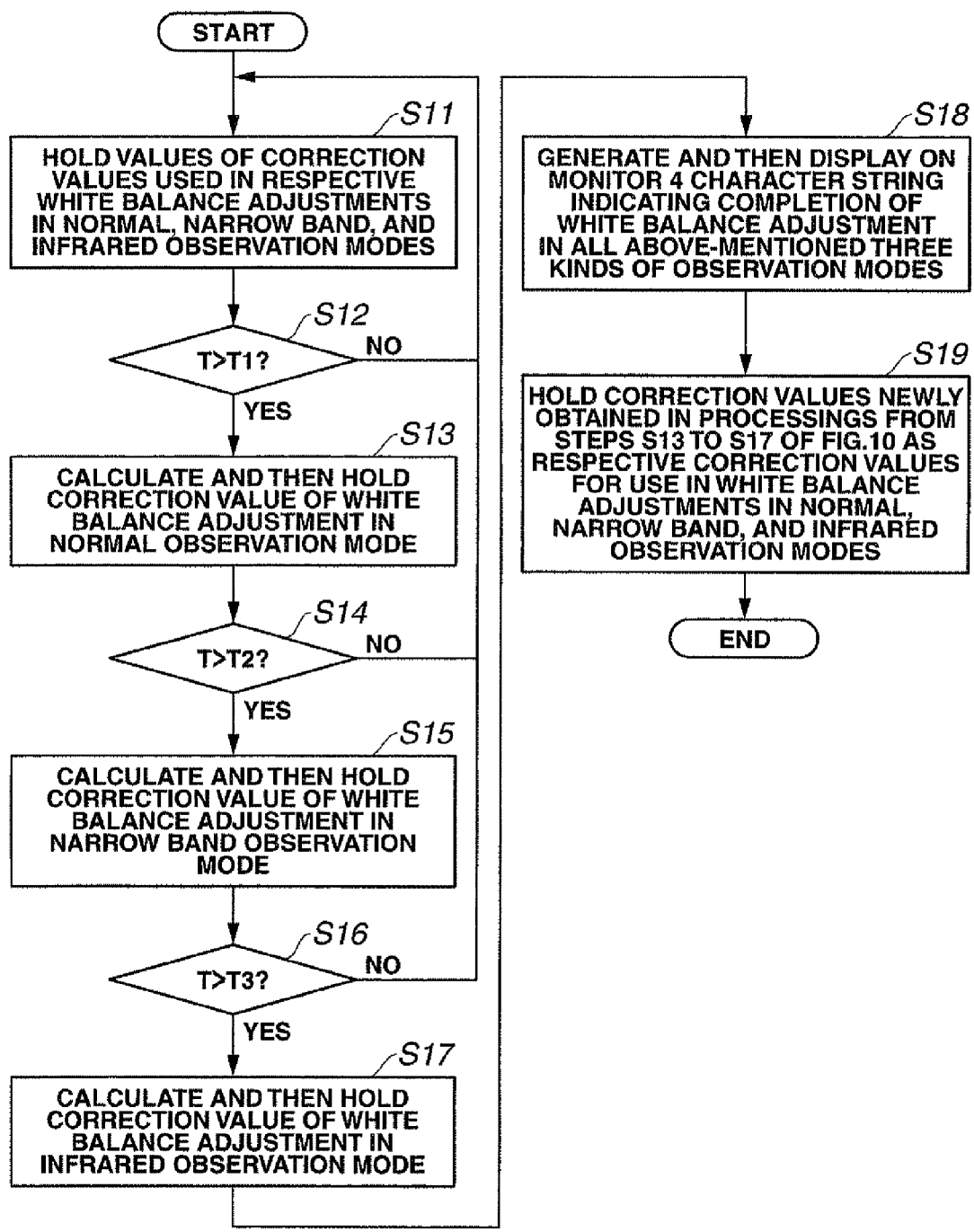
FIG. 10 is a flow chart showing a processing to be performed in color balance adjustment by the image processing apparatus of the present embodiment, which is different from the processing shown in FIG. 8.
Figure 11:
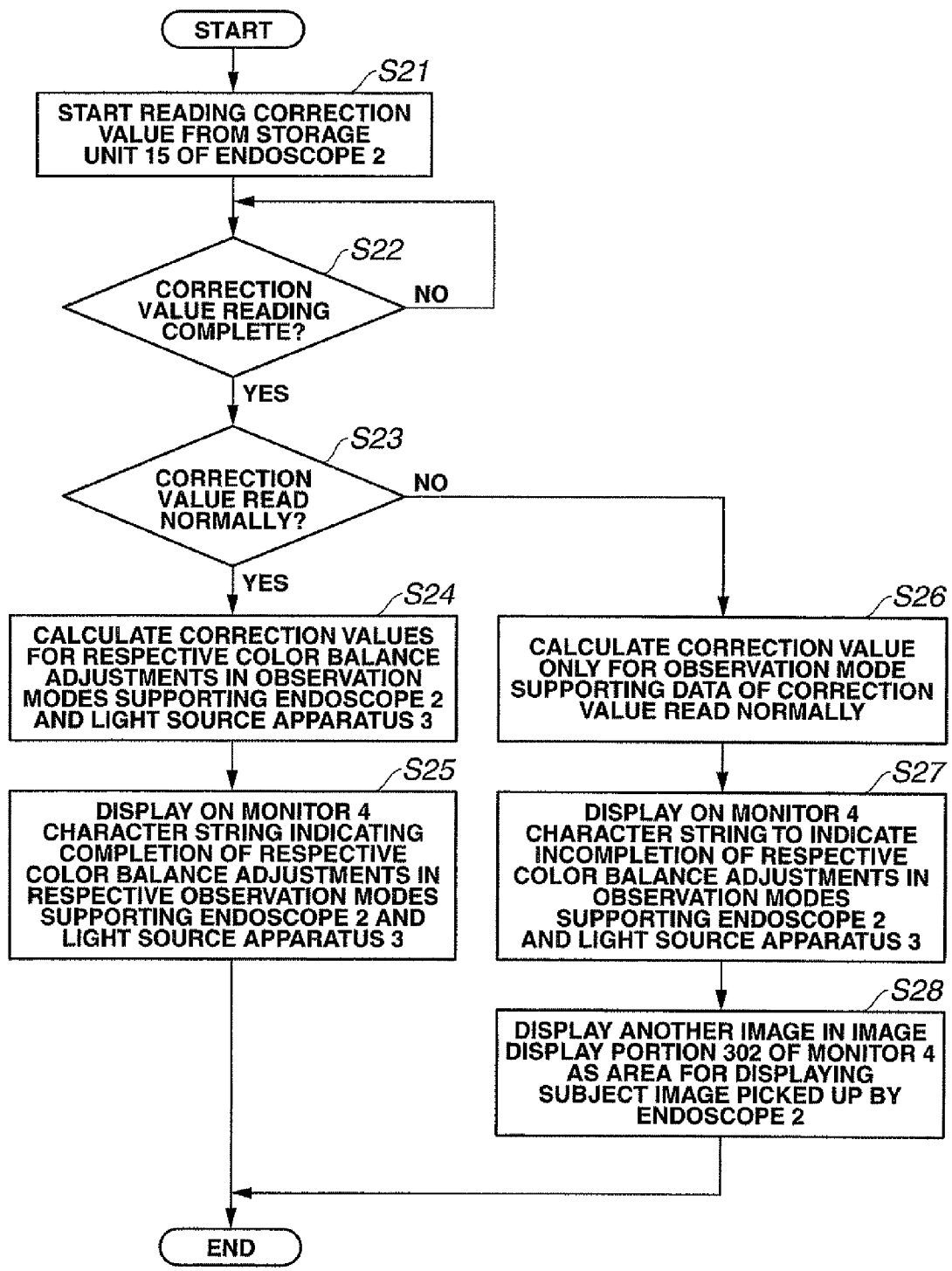
FIG. 11 is a flow chart showing a processing performed in color balance adjustment by the image processing apparatus of the present embodiment, which is different from the processings shown in FIGS. 8 and 10.
Figure 12:
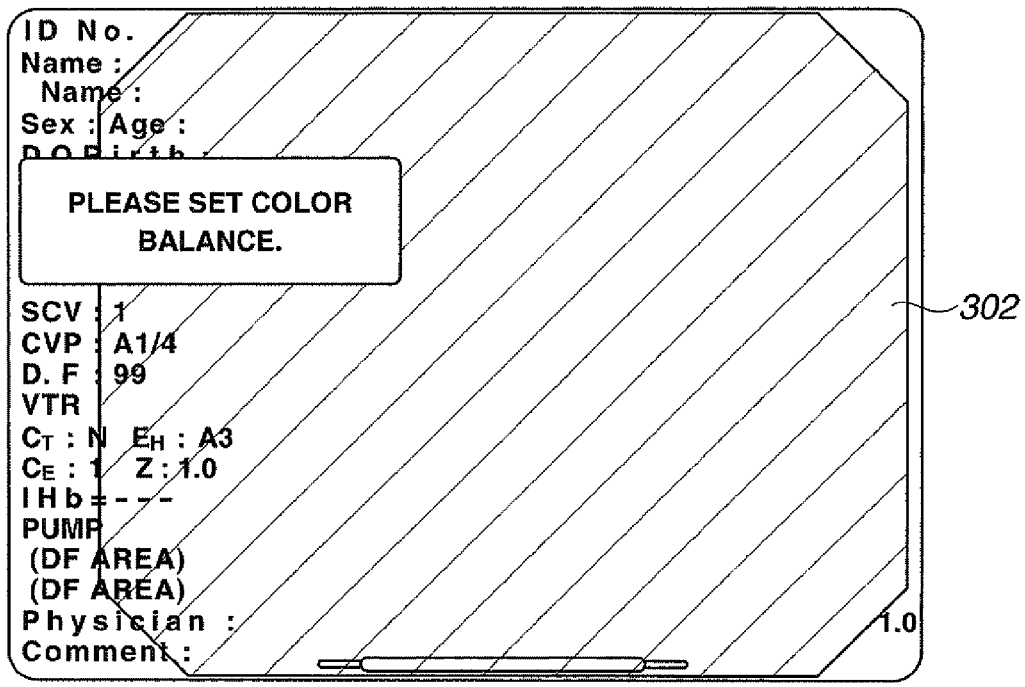
FIG. 12 is a view showing an exemplary image to be displayed on the monitor by the image processing apparatus of the present embodiment when performing the processing shown in FIG. 11.
Figure 13:
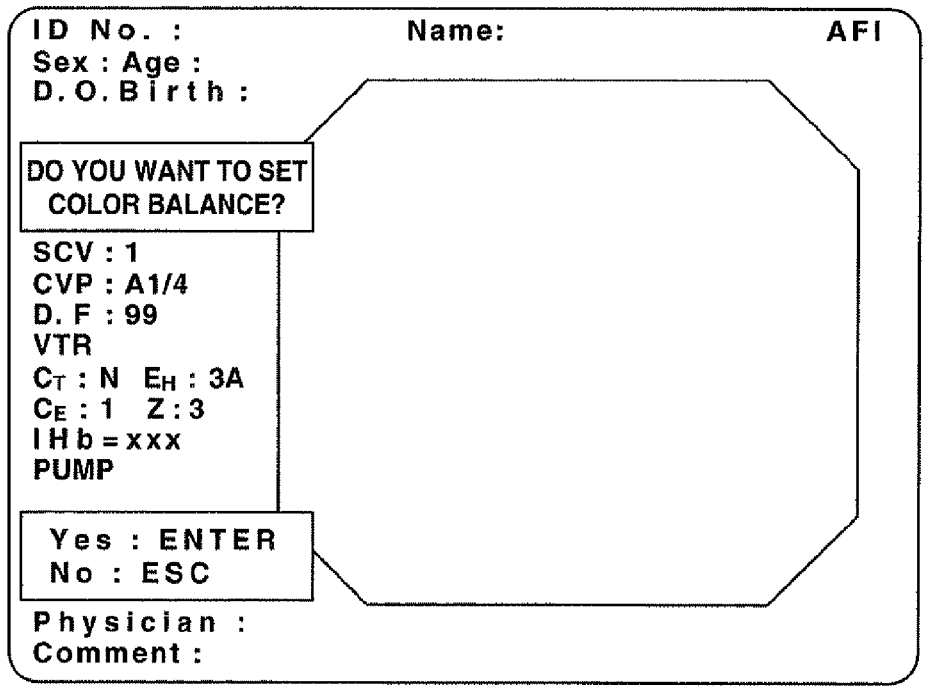
FIG. 13 is a view showing an exemplary character string inquiring of a user whether or not to perform color balance adjustment, which is displayed on the monitor by the image processing apparatus of the present embodiment.
Figure 14:
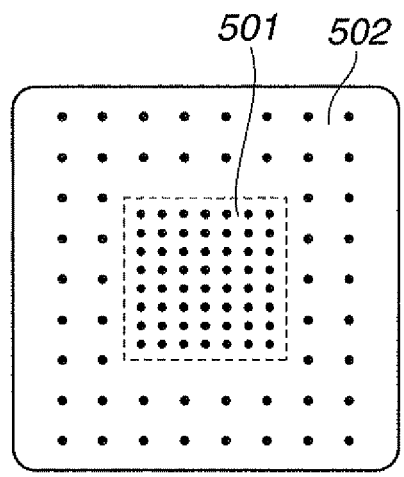
FIG. 14 is a view showing exemplary pixels to be sampled by the image processing apparatus of the present embodiment when calculating a correction value to perform color balance adjustment.
Figure 15:
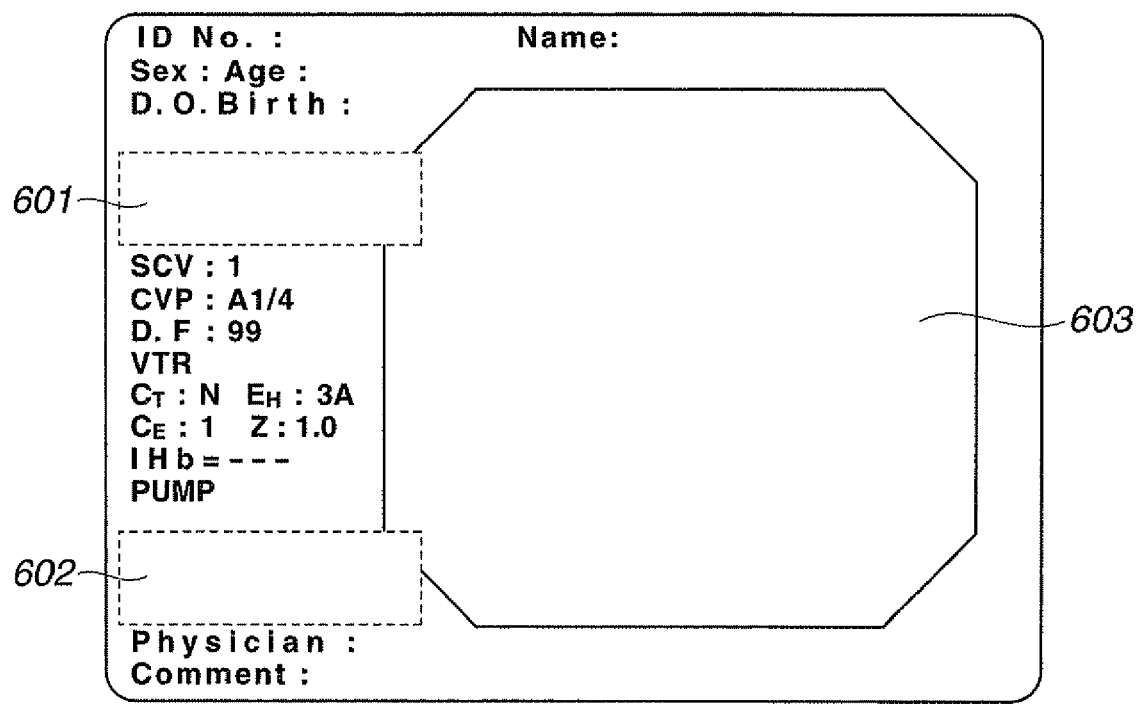
FIG. 15 is a view showing an exemplary standard image to be displayed on the monitor when observation is performed using the endoscope apparatus of the present embodiment.
Figure 16:
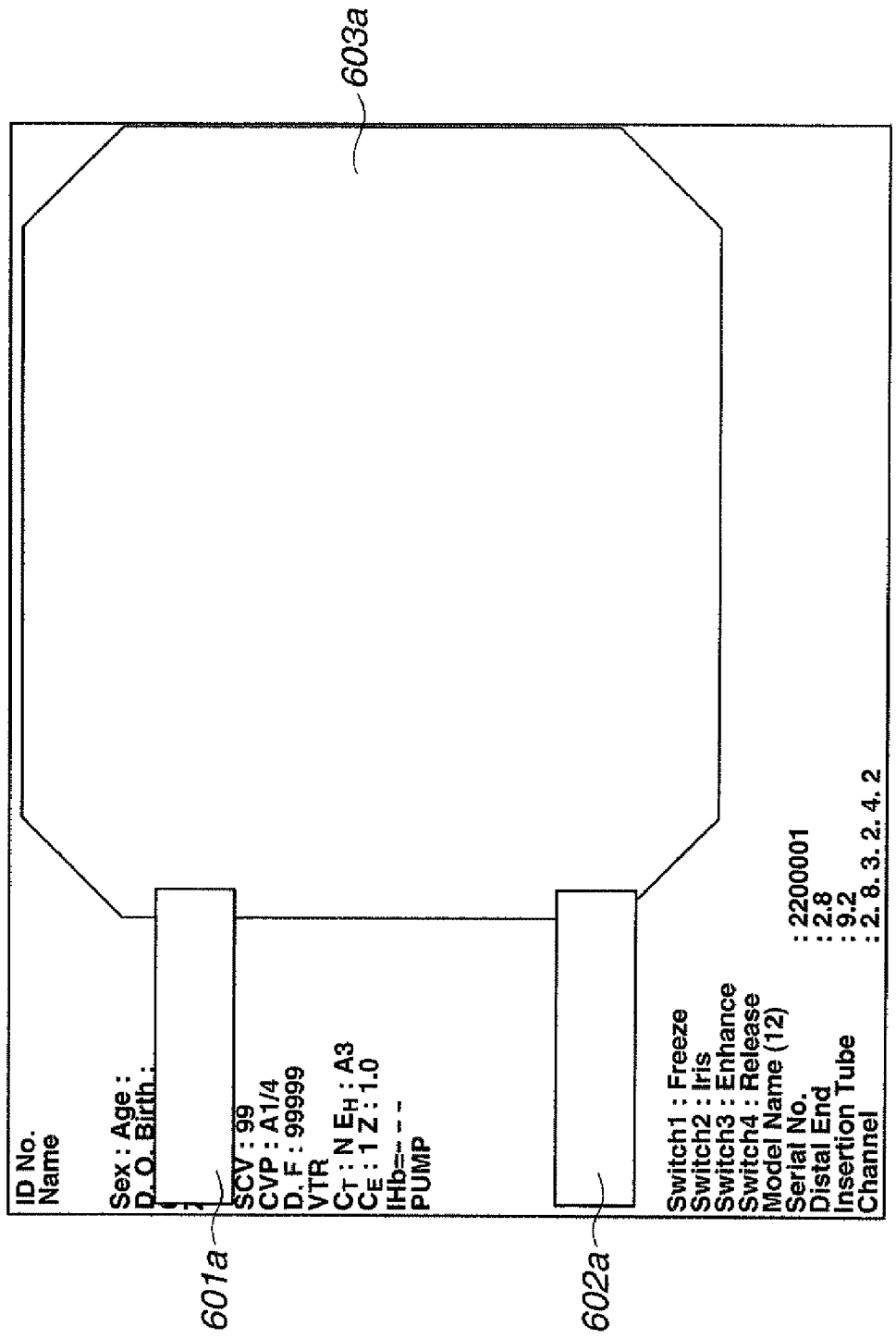
FIG. 16 is a view showing an exemplary high-definition image to be displayed on the monitor when observation is performed using the endoscope apparatus of the present embodiment.

An embodiment of the present invention is described with reference to the drawings, wherein: FIG. 1 is a block diagram showing an exemplary configuration of an endoscope apparatus of the present embodiment; FIG. 2 is a view showing correlation between bands and transmissivities of an RGB filter included by a light source apparatus of the endoscope apparatus of the present embodiment; FIG. 3 is a view showing correlation between bands and transmissivities of a fluorescent light observation filter included by the light source apparatus of the endoscope apparatus of the present embodiment; FIG. 4 is a view showing an operation panel provided to an image processing apparatus configuring the endoscope apparatus of the present embodiment; FIG. 5 is a view showing an appearance of an endoscope color-balance-adjustment tool used for the endoscope apparatus of the present embodiment; FIG. 6 is a section view of the endoscope color-balance-adjustment tool shown in FIG. 5; FIG. 7 is a view showing an exemplary correction value input screen displayed on a monitor by the image processing apparatus of the present embodiment; FIG. 8 is a flow chart showing an exemplary processing to be performed in color balance adjustment by the image processing apparatus of the present embodiment; FIG. 9 is a view showing an exemplary menu screen displayed on the monitor, in the endoscope apparatus of the present embodiment; FIG. 10 is a flow chart showing a processing to be performed in color balance adjustment by the image processing apparatus of the present embodiment, which is different from the processing shown in FIG. 8; FIG. 11 is a flow chart showing a processing performed in color balance adjustment by the image processing apparatus of the present embodiment, which is different from the processings shown in FIGS. 8 and 10; FIG. 12 is a view showing an exemplary image to be displayed on the monitor by the image processing apparatus of the present embodiment when performing the processing shown in FIG. 11; FIG. 13 is a view showing an exemplary character string inquiring of a user whether or not to perform color balance adjustment, which is displayed on the monitor by the image processing apparatus of the present embodiment; FIG. 14 is a view showing exemplary pixels to be sampled by the image processing apparatus of the present embodiment when calculating a correction value to perform color balance adjustment; FIG. 15 is a view showing an exemplary standard image to be displayed on the monitor when observation is performed using the endoscope apparatus of the present embodiment; and FIG. 16 is a view showing an exemplary high-definition image to be displayed on the monitor when observation is performed using the endoscope apparatus of the present embodiment.

As shown in FIG. 1, main part of an endoscope apparatus 1 is configured by an endoscope 2 for picking up a subject image, a light source apparatus 3, a monitor 4 serving as a display apparatus for displaying a subject image picked up by the endoscope 2, and an image processing apparatus 5.

The endoscope 2 includes inside thereof an image pickup unit 11, a light guide 12, and a storage unit 15 which is configured as a memory to/from which information can be freely written/read by means of a signal such as an electrical signal, and which has therein prewritten information such as type of the endoscope 2 and a value at factory shipment of a correction value used in color balance adjustment to be described below. The endoscope 2 also includes, on an outer covering surface thereof, an operation switch 13 and a connector 14 which is detachably connected to a connector 31 of the image processing apparatus 5 via a cable or the like not shown.

The image pickup unit 11, which is provided in a distal end portion of the endoscope 2, includes an image pickup device such as CCD not shown (in FIG. 1) and an object optical system such as a lens not shown (in FIG. 1), picks up a subject image, and outputs the picked up subject image as an image signal.

The light guide 12, which is formed by quarts fibers or the like, is provided to be inserted inside the endoscope 2, with one end disposed in the distal end portion of the endoscope 2 and the other end disposed to be connected to the light source apparatus 3. With such a configuration, the light guide 12 leads lights radiated from the light source apparatus 3 to the distal end portion of the endoscope 2.

The operation switch 13, when operated by a user, outputs as a signal an instruction to start and stop picking up a subject image to, for example, the image pickup unit 11 of the endoscope 2 via the image processing apparatus 5.

The light source apparatus 3 includes therein a light source unit 21 comprised of a light source such as a xenon lamp, for radiating white light, an RGB filter 22, a fluorescent light observation filter 23, a condensing lens 24 for condensing irradiation light radiated from the light source unit 21 onto an incident end surface of the light guide 12, a filter control unit 25 for driving and controlling the RGB filter 22 and the fluorescent light observation filter 23, and a storage unit 27 which is configured as a memory to/from which information can be freely written/read by means of a signal such as an electrical signal, and which has therein prewritten information such as type and serial number of the light source apparatus 3. The light source apparatus 3 includes, on an outer covering surface thereof, an operation panel 26 and a connector 28 which is detachably connected to a connector 43 of the image processing apparatus 5 via a cable or the like not shown.

The RGB filter 22 includes an R filter which transmits a light having a red wavelength band, a G filter which transmits a light having a green wavelength band, and a B filter which transmits a light having a blue wavelength band. These three kinds of filters included by the RGB filter 22 are formed to have correlation between wavelength bands and transmissivities as shown in FIG. 2. The RGB filter 22 has a configuration such that, when the RGB filter 22 is disposed on an irradiation optical path of the light source unit 21 by the filter control unit 25, the R, G and B filters are inserted generally continuously on the irradiation optical path. With the RGB filter 22 having the above-mentioned configuration, when performing the normal observation, the light source apparatus 3 radiates normal observation irradiation light as first irradiation light, irradiating, in a frame sequential manner, a light having the red wavelength band, a light having the green wavelength band, and a light having the blue wavelength band.

The fluorescent light observation filter 23 includes an Ex filter for transmitting a light including a predetermined wavelength band among the blue wavelength band, that excites fluorescent light from the subject; a ref1 filter for transmitting a light having a partial wavelength band among the green wavelength band; and a ref2 filter for transmitting a light having a partial wavelength band among the red wavelength band. These three kinds of filters included by the fluorescent light observation filter 23 are formed to have correlation between wavelength bands and transmissivities as shown in FIG. 3. The fluorescent light observation filter 23 has a configuration such that, when the fluorescent light observation filter 23 is disposed on an irradiation optical path of the light source unit 21 by the filter control unit 25, the Ex, ref1 and ref2 filters are inserted generally continuously on the irradiation optical path. With the fluorescent light observation filter 23 having the above-mentioned configuration, when performing the fluorescent light observation, the light source apparatus 3 radiates a fluorescent light observation irradiation light as a second irradiation light, which irradiates, in a frame sequential manner, an excitation light as a light having the predetermined wavelength band that excites fluorescent light from the subject, a ref1 light as a light having a partial wavelength band of the green wavelength band, and a ref2 light as a light having a partial wavelength band of the red wavelength band.

The filter control unit 25 performs a control such as, for example, to dispose one of the RGB filter 22 and the fluorescent light observation filter 23 on the irradiation optical path of the light source unit 21 and thereafter drive to rotate the disposed filter. When the filter control unit 25 performs such a control, the light source apparatus 3 radiates either the normal observation irradiation light or the fluorescent light observation irradiation light.

The operation panel 26 includes a normal observation mode switch not shown for switching the irradiation light radiated from the light source apparatus 3 to the normal observation irradiation light, and a fluorescent light observation mode switch not shown for switching the irradiation light radiated from the light source apparatus 3 to the fluorescent light observation irradiation light. When the user performs a change-over operation of these switches, a signal including a control instruction to change the filter to be disposed on the irradiation optical path of the light source unit 21 is outputted from the operation panel 26 to the filter control unit 25. The signal including the control instruction is outputted also to the image processing apparatus 5 via the filter control unit 25. This allows the image processing apparatus 5 to detect whether the irradiation light radiated from the light source apparatus 3 is the normal observation irradiation light or the fluorescent light observation irradiation light.

Note that the light source apparatus 3 is not limited to radiating, as irradiation light, only the two kinds of irradiation lights: the normal observation irradiation light and the fluorescent light observation irradiation light. Besides the two kinds of irradiation lights, the light source apparatus 3 may radiate, for example, infrared observation irradiation light including a near infrared wavelength band, or narrow band observation irradiation light comprised of red, green and blue narrow band lights.

The image processing apparatus 5 includes inside thereof a CCD drive unit 32 as a driving circuit for driving a CCD not shown (in FIG. 1) provided in the image pickup unit 11, an image signal input unit 33, a color balance process unit 34, an image signal output unit 35, and an image processing apparatus control unit 42, as a control circuit comprised of a CPU and others, for controlling each of the endoscope 2, the light source apparatus 3, and the image processing apparatus 5. The image processing apparatus 5 includes, on an outer covering surface thereof a connector 31 detachably connected to the connector 14 of the endoscope 2 via a cable or the like not shown, an operation panel 41, and a connector 43 detachably connected to the connector 28 of the light source apparatus 3 via a cable or the like not shown.

The image signal input unit 33 is configured by circuits such as of an A/D converter not shown, and performs processings such as noise removal and A/D conversion on an image signal of a subject image outputted from the image pickup unit 11 of the endoscope 2, thereafter outputting an image signal after being subjected to the processings.

When performing a color balance adjustment supporting each observation mode of the endoscope apparatus 1, the color balance process unit 34 performs, on the image signal outputted from the image signal input unit 33, brightness correction based on the color balance adjustment, and outputs an image signal subjected to the processing. Note that, in an observation mode such as the normal light observation mode, which is an observation mode other than the fluorescent light observation mode, the color balance process unit 34 of the image processing apparatus 5 is assumed to perform the white balance adjustment as one of color balance adjustments. In the fluorescent light observation mode, the color balance process unit 34 of the image processing apparatus 5 is assumed to perform a color balance adjustment different from the above-mentioned white balance adjustment. In other words, in the present embodiment, unless otherwise specified, color balance adjustment is assumed to indicate both or either one of the color balance adjustment in the fluorescent light observation mode and the white balance adjustment in an observation mode other than the fluorescent light observation mode.

The image signal output unit 35 includes circuits such as of an RGB multiplexer and D/A converter not shown. The image signal output unit 35 thus configured performs, on the image signal outputted from the color balance process unit 34, processings such as assigning signal components included in the image signal to R, G and B three color channels and D/A conversion, thereafter outputting an image signal assigned to these three color channels as a synchronized RGB image signal. Then, the monitor 4 color-displays the subject image picked up by the image pickup unit 11, based on the RGB image signal outputted from the image signal output unit 35. The image signal output unit 35 includes, besides the above-mentioned circuits, an image generating circuit not shown to generate, for example, an image of a system menu screen of the endoscope apparatus 1, an image of a correction value input screen to be described later, and so on, based on a control signal from the image processing apparatus control unit 42.

The operation panel 41 includes a color balance switch 101, as shown in FIG. 4. When the user operates the color balance switch 101, an instruction signal with a control instruction to perform color balance adjustment is outputted to the image processing apparatus control unit 42, in the endoscope apparatus 1. The operation panel 41 further includes a color balance setting incompletion display portion 102 to indicate that the color balance setting is incomplete, and a color balance setting completion display portion 103 to indicate that color balance setting is complete, as shown in FIG. 4.

The color balance setting incompletion display portion 102 and the color balance setting completion display portion 103 as notifying portions indicate whether or not color balance adjustment has been performed, by, for example, reversing the lighting state of the LED according to setting state of color balance.

As shown in FIG. 5, the endoscope color-balance-adjustment tool 201, as a fluorescent light observation color balance chart, is configured as, for example, a tubular body with a generally cylindrical shape having an outer circumferential surface formed by a light-shielding member such as of metal or resin of macromolecule system, and a structure with one end closed. The endoscope color-balance-adjustment tool 201 has an aperture portion 201a with an inner diameter so as to allow insertion of the distal end portion of the endoscope 2, and an internal space 201b that communicates with the aperture portion 201a. The inner circumferential surface of the endoscope color-balance-adjustment tool 201, which forms the internal space 201b, is configured such that at least an end surface portion 201c has a fluorescent light generating portion formed by a fluorescent member such as a white paint, and farther that the inner circumferential surface covers parts other than the aperture portion 201a. In other words, the fluorescent light generating portion provided on the inner circumferential surface of the endoscope color-balance-adjustment tool 201 is provided to be included in at least a part of an image of the inner circumferential surface picked up by the image pickup unit 11.

As shown in FIG. 5, on an outer surface of the endoscope color-balance-adjustment tool 201, there is provided a correction value display portion 201d showing a correction value WBCAF to be used in color balance adjustment described below. Note that the correction value WBCAF is a value that is determined at the time of manufacture or factory shipment as a relative value when reference intensity of the fluorescent light emitted from the inner circumferential surface of the endoscope color-balance-adjustment tool is provided as "1.0". The correction value WBCAF is also a value shown as a correction value to correct variation in intensity of the fluorescent light emitted from the inner circumferential surface of the endoscope color-balance-adjustment tool 201.

Incidentally, the state where the distal end portion of the endoscope 2 is inserted into the internal space 201b from the aperture portion 201a of the endoscope color-balance-adjustment tool 201 is as shown in FIG. 6. When excitation light is radiated from the light guide 12 in such a state, an object optical system 11a of the image pickup unit 11 condenses the fluorescent light emitted from the fluorescent member on the inner circumferential surface of the endoscope color-balance-adjustment tool 201. Then, the image pickup device 11b of the image pickup unit 11 provided at an image formation position of the object optical system 11a picks up an image of the inner circumferential surface of the endoscope color-balance-adjustment tool 201 obtained by the object optical system 11a, thereafter converting the picked up image into an image signal to be outputted.

Next, workings of the endoscope apparatus 1 of the present embodiment are described.

First, the user connects parts that configure the main part of the endoscope apparatus 1, i.e., the endoscope 2, the light source apparatus 3, the monitor 4, and the image processing apparatus 5, and then turns on power of each of the parts of the endoscope apparatus 1 for activation. In such a state, the CCD drive unit 32 drives the CCD not shown (in FIG. 1) provided in the image pickup unit 11. Further in this state, the image processing apparatus control unit 42 reads pieces of type information of the endoscope 2 and the light source apparatus 3 that are written, respectively, in the storage unit 15 of the endoscope 2 and the storage unit 27 of the light source apparatus 3, to detect what kinds of observation modes the endoscope 2 and the light source apparatus 3 support.

The user next turns on the fluorescent light observation mode switch of the light source apparatus 3 to cause fluorescent light observation irradiation light to be radiated from the light source apparatus 3. After having turned on the fluorescent light observation mode switch of the light source apparatus 3, the user inserts the distal end portion of the endoscope 2 into the internal space 201b from the aperture portion 201a of the endoscope color-balance-adjustment tool 201, such that, for example, the distal end portion of the endoscope 2 is disposed at a position as shown in FIG. 6 in the internal space 201b of the endoscope color-balance-adjustment tool 201.

When the fluorescent light observation mode switch is turned on through the operation panel 26 of the light source apparatus 3, a mode change-over signal is outputted to the image processing apparatus control unit 42 via the filter control unit 25 and the connector 28. The image processing apparatus control unit 42 changes each part of the image processing apparatus 5 over to the fluorescent light observation mode, based on the mode change-over signal outputted from the operation panel 26.

Thereafter, when the user performs the operation as mentioned above, the image pickup unit 11 of the endoscope 2 picks up a subject image of the subject illuminated by the excitation light of the fluorescent light observation irradiation light, the subject image being comprised of an image of the fluorescent light emitted by the fluorescent member on the inner circumferential surface of the endoscope color-balance-adjustment tool 201, an image of reflection light of the ref1 light, and an image of reflection light of the ref2 light, and then outputs the picked up subject image as an image signal. The image signal outputted from the image pickup unit 11 is inputted to the image signal input unit 33 of the image processing apparatus 5.

In such a state, when, for example, the user operates the color balance switch 101 of the operation panel 41, the each part of the image processing apparatus 5 performs color balance adjustment in the fluorescent light observation mode by a method described below. Note that the initial state, as a state before the below-described processings are performed, is assumed to be a state right before the color balance switch 101 is operated.

When the color balance switch 101 is operated by the user and outputs an instruction signal to perform color balance adjustment in the fluorescent light observation mode (step S1 of FIG. 8), the image processing apparatus control unit 42 outputs a control signal for displaying, for example, the correction value input screen as shown in FIG. 7 on the monitor 4, to the image signal output unit 35 based on the instruction signal. The image signal output unit 35 generates and displays a correction value input screen as shown in FIG. 7 on the monitor 4 based on the control signal outputted from the image processing apparatus control unit 42 (step S2 of FIG. 8).

Note that the image processing apparatus control unit 42 may control the image signal output unit 35 to display on the monitor 4, for example, a character string inquiring of the user whether or not to perform color balance adjustment in the fluorescent light observation mode, during the interval between when the processing shown in step S1 of FIG. 8 is performed and when the processing shown in step S2 of FIG. 8 is performed.

More specifically, the image processing apparatus control unit 42, on detecting an instruction signal outputted from the color balance switch 101, controls the image signal output unit 35 to display on the monitor 4, for example, character strings reading "Should color balance setting be performed?", "Yes: Enter", and "No: Esc". The image signal output unit 35 generates and displays a screen as shown in FIG. 13 on the monitor 4, based on the control content of the image processing apparatus control unit 42.

Thereafter, the image processing apparatus control unit 42, on detecting, for example, pushing down of an "Esc" key of a keyboard not shown connected to the image processing apparatus 5, brings the each part of the image processing apparatus 5 into the state right before the color balance switch 101 is operated. Also, the image processing apparatus control unit 42, on detecting, for example, pushing down of an "Enter" key of the keyboard not shown connected to the image processing apparatus 5, outputs to the image signal output unit 35, for example, a control signal to display the correction value input screen as shown in FIG. 7 on the monitor 4. The image signal output unit 35 then generates and displays a correction value input screen as shown in FIG. 7 on the monitor 4, based on the control signal outputted from the image processing apparatus control unit 42.

In the state where the correction value input screen as shown in FIG. 7 is displayed on the monitor 4, the user uses, for example, a keyboard not shown connected to the image processing apparatus 5, or the like, to input to the correction value input portion 301 the correction value WBCAF which is displayed in the correction value display portion 201d of the endoscope color-balance-adjustment tool 201. On a part at a lower end of the monitor 4, there is displayed an operation guiding portion 301A to show a list of operations the user can perform on the correction value input screen as shown in FIG. 7. Note that, on the correction value input screen as shown in FIG. 7, there are displayed character strings reading, for example, "Please prepare an AFI color balance cap." and "Please input a cap correction value." as messages to urge the user to make preparation for the operation about inputting the correction value WBCAF to the correction value input portion 301, along with the correction value input portion 301 and the operation guiding portion 301A.

The correction value input portion 301 of the correction value input screen shown in FIG. 7 is configured such that user operation of "←" and "→" keys of the keyboard not shown connected to the image processing apparatus 5 sequentially changes the displayed value. For example, when the user pushes down the "←" and "→" keys of the keyboard not shown, correction values "0.5", "0.6", "0.7", "0.8", "0.9", "1.0", "-", "1.0", "1.1", "1.2", "1.3", "1.4" and "1.5" are sequentially displayed in the correction value input portion 301. Note that, in the initial state, "-" is assumed to be displayed in the correction value input portion 301. Furthermore, the values mentioned above as correction values are not limited to those selected by the "←" and "→" keys of the keyboard not shown, but may be those directly inputted to the correction value input portion 301 by, for example, a numeric key of the keyboard not shown.

Thereafter, the image processing apparatus control unit 42 judges whether or not the correction value WBCAF is inputted to the correction value input portion 301.

For example, if the "Esc" key of the keyboard not shown is pushed down, or if the "Enter" key of the keyboard not shown is pushed down in a state where the "-" is displayed in the correction value input portion 301, the image processing apparatus control unit 42 judges that the correction value WBCAF is not inputted to the correction value input portion 301 (step S3 of FIG. 8). The image processing apparatus control unit 42 then interrupts processing of the color balance adjustment in the fluorescent light observation mode, brings each of the endoscope 2, the light source apparatus 3, and the image processing apparatus 5 into the initial state, and maintains the initial state until the color balance switch 101 is reoperated by the user (step S1 of FIG. 8).

If, for example, any correction value (except "-") is selected by the "←" and "→" keys of the keyboard not shown, followed by pushing down of the "Enter" key, then the image processing apparatus control unit 42 judges that the correction value WBCAF is inputted to the correction value input portion 301 (step S3 of FIG. 8).

Note that the correction value WBCAF may be associated to photometry mode and light adjustment level that are set by the image processing apparatus control unit 42 in performing the following processing. In that case, the image processing apparatus control unit 42 controls the image processing output unit 35 so as to turn the photometry mode and the light adjustment level as brightness of the entire screen into a predetermined state, based on the value of the selected correction value WBCAF.

More specifically, if, for example, "1.0" is selected as the correction value WBCAF, the image processing apparatus control unit 42 judges that intensity of the fluorescent light emitted from the inner circumferential surface of the endoscope color-balance-adjustment tool 201 is generally the same as the reference intensity of the fluorescent light, and controls the image processing output unit 35 to set the photometry mode to automatic and the light adjustment level value to "0". If, for example, "1.3" is selected as the correction value WBCAF, the image processing apparatus control unit 42 judges that intensity of the fluorescent light emitted from the inner circumferential surface of the endoscope color-balance-adjustment tool 201 is smaller than the reference intensity of the fluorescent light, and controls the image processing output unit 35 to set the photometry mode to automatic and the light adjustment level value to "+3". Note that the image processing apparatus control unit 42, when performing the above-mentioned control on the image processing output unit 35, invalidates, while temporarily holding, the photometry mode and light adjustment level value preset by the user. After having performed the above-mentioned control on the image processing output unit 35, the image processing apparatus control unit 42 again validates the photometry mode and light adjustment level value preset by the user, which are being held.

Thereafter, the image processing apparatus control unit 42 calculates a mean value WBAF of brightness values for one screen of the image of the fluorescent light emitted by the fluorescent member on the inner circumferential surface of the endoscope color-balance-adjustment tool 201 (step S4 of FIG. 8). The image processing apparatus control unit 42 further calculates a mean value WBR of brightness values for one screen of the image of the reflection light of the ref2 light on the inner circumferential surface of the endoscope color-balance-adjustment tool 201 (step S4 of FIG. 8).

Then, based on the mean value WBAF of the brightness values for one screen of the fluorescent light image, the mean value WBR of the brightness values for one screen of the reflection light image, and the correction value WBCAF inputted by the user, the image processing apparatus control unit 42 calculates, using the following mathematical expressions (1) and (2), a correction value WBKAF for the fluorescent light image and a correction value WBKR for the image of the reflection light of the ref2 light, as values of coefficients to be used for color balance adjustment in the fluorescent light observation mode (step S5 of FIG. 8).

$$WBKAF = 1 \tag{1}$$

$$WBKR = WBAF / (WBR \times WBCAF) \tag{2}$$

The image processing apparatus control unit 42 then outputs the correction value WBKAF for the fluorescent light image and the correction value WBKR for the image of the reflection light of the ref2 light, calculated, to the color balance process unit 34.

The color balance process unit 34 performs brightness correction on the fluorescent light image and the image of the reflection light of the ref2 light, based on the correction value WBKAF for the fluorescent light image, the correction value WBKR for the image of the reflection light of the ref2 light, and the image signal inputted from the image signal input unit 33 (step S6 of FIG. 8). After having performed the brightness correction based on the correction values WBKAF and WBKR, the color balance process unit 34 outputs the image signal after being subjected to the correction to the image signal output unit 35. Note that, until a new correction value is outputted from the image processing apparatus control unit 42, the color balance process unit 34 is assumed to hold the correction values WBKAF and WBKR, and perform brightness correction on image signals inputted from the image signal input unit 33 based on those two correction values.

The image signal output unit 35 assigns the image signal of the fluorescent light image to the G channel, the image signal of the image of the reflection light of the ref1 light to the R channel, and the image signal of the image of the reflection light of the ref2 light to the B channel, based on the image signal outputted from the color balance process unit 34, and thereafter outputs the image signals assigned to the three color channels as a synchronized RGB image signal (step S7 of FIG. 8).

The monitor 4 then color-displays the fluorescent light image picked up by the image pickup unit 11, based on the RGB image signal outputted from the image signal output unit 35.

Note that the correction value input screen, into which a correction value is inputted, is not limited to the one shown in FIG. 7, which is not displayed until the color balance switch 101 is operated. Alternatively, the correction value input screen may be such that, for example, the correction value input portion 301a is displayed as a part of a system menu screen of the endoscope apparatus 1 as shown in FIG. 9. This allows the user to input the value displayed in the correction value display portion 201d of the endoscope color-balance-adjustment tool 201 in advance before performing color balance adjustment supporting each observation mode of the endoscope apparatus 1. As a result, the user can decentralize the load of works to be performed in color balance adjustment supporting each observation mode.

In addition, a list of operations to be performed by the user using the keyboard not shown in the above-mentioned processings is displayed as a part of the correction value input screen as shown in FIG. 7 on, for example, the operation guiding portion 301A. Therefore, the user can input the correction value WBCAF used in color balance adjustment in the fluorescent light observation mode without turning the eyes away from the monitor 4, while referring to an operation method displayed on the operation guiding portion 301A.

Furthermore, when performing color balance adjustment in the fluorescent light observation mode, the image processing apparatus 5 may be configured so as, for example, to sample the image signal of the image of the reflection light of the ref1 light outputted from the endoscope 2, in a manner to focusedly sample pixels in a part close to the center of an image based on the image signal, and thereafter calculate a correction value to perform color balance adjustment in the fluorescent light observation mode, based on brightness value of sampled predetermined number of pixels.

More specifically, the image processing apparatus control unit 42 of the image processing apparatus 5 first samples, for example, 80% of the predetermined number of pixels from a center portion 501 and 20% of the predetermined number of pixels from a peripheral portion 502 in the image based on the image signal outputted from the endoscope 2, as shown in FIG. 14. The image processing apparatus control unit 42 then detects respective brightness values of the sampled predetermined number of pixels, and holds the detected values. Further, the image processing apparatus control unit 42 specifies, of the held brightness values of the predetermined number of pixels, pixels with brightness values not less than 210 and pixels with brightness values not more than 15, and excludes the specified pixels from processing performed thereafter. The image processing apparatus control unit 42 calculates a mean value of the brightness values of the non-excluded remaining pixels, thereafter calculating, based on the mean value, a correction value to perform color balance adjustment in the fluorescent light observation mode.

Note that, in the above-mentioned processing, if the number of the non-excluded remaining pixels, in the specifying and excluding of pixels with brightness values not less than 210 and not more than 15, is not more than 30% of the predetermined pixel number, the image processing apparatus control unit 42 controls the image signal output unit 35 to display on the monitor 4 a character string indicating failure of color balance processing in the fluorescent light observation mode, without renewing the correction value to perform color balance adjustment in the fluorescent light observation mode.

As mentioned above, the endoscope apparatus 1 of the present embodiment can perform color balance adjustment that is based on the correction value WBCAF that is based on variation in fluorescent intensity of the fluorescent material provided on the inner circumferential surface of the endoscope color-balance-adjustment tool 201, among characteristic variations occurring with the endoscope color-balance-adjustment tool 201. Accordingly, the endoscope apparatus 1 of the present embodiment can obtain a good observation image.

Note that, although the aforementioned processings performed by the image processing apparatus 5 are described to be performed when the light source apparatus 3 has a function to emit only two kinds of irradiation lights: the normal observation irradiation light and the fluorescent light observation irradiation light, no limitation is placed thereon. For example, if the light source apparatus 3 further includes a function to emit, for example, infrared observation irradiation light supporting an infrared observation mode and narrow band observation irradiation light supporting a narrow band observation mode, in addition to the above-mentioned two kinds of irradiation lights, then the image processing apparatus 5 may perform the below-described processing in white balance adjustments respectively supporting the observation modes. Note that the below-described processings for the each part of the image processing apparatus 5 are assumed to be performed in the case where white balance adjustments respectively supporting the plurality of observation modes are performed in a sequential and continuous manner with respect to the plurality of observation modes, using the same endoscope color-balance-adjustment tool.

In the initial action after activation, the image processing apparatus control unit 42 of the image processing apparatus 5 reads, from the storage unit 15 of the endoscope 2, correction values to be used in respective white balance adjustments supporting the three kinds of observation modes associated to the connected light source apparatus 3, i.e., the normal observation mode, the narrow band observation mode, and the infrared observation mode. Thereafter, the image processing apparatus control unit 42 performs control to cause the color balance process unit 34 to hold values of the respective correction values in the three kinds of observation modes. The color balance process unit 34 holds the values of the respective correction values in the above-mentioned three kinds of observation modes, based on the control performed by the image processing apparatus control unit 42 (step S11 of FIG. 10). Note that the image processing apparatus control unit 42, if detecting that in the storage unit 15 of the endoscope 2 there do not exist the respective correction values in the three kinds of observation modes, associated to the light source apparatus 3 connected, may define correction values held by the color balance process unit 34 as initial values.

Then, the image processing apparatus control unit 42, if detects that a time period T during which the instruction signal is continuously outputted by continuous pushing down of the color balance switch 101 is greater than a time period T1 (step S12 of FIG. 10), obtains a mean value of brightness values for one screen in the normal observation mode, calculates a correction value for the white balance adjustment in the normal observation mode, and thereafter holds the calculated correction value (step S13 of FIG. 10).

Further, the image processing apparatus control unit 42, if detects that the time period T during which the instruction signal is continuously outputted by continuous pushing down of the color balance switch 101 is greater than a time period T2 (T1<T2) (step S14 of FIG. 10), obtains a mean value of brightness values for one screen in the narrow band observation mode, calculates a correction value for the white balance adjustment in the narrow band observation mode, thereafter holds the calculated correction value (step S15 of FIG. 10).

Still further, the image processing apparatus control unit 42, if detects that the time period T during which the instruction signal is continuously outputted by continuous pushing down of the color balance switch 101 is greater than a time period T3 (T2<T3) (step S16 of FIG. 10), obtains a mean value of brightness values for one screen in the infrared observation mode, calculates a correction value for the white balance adjustment in the infrared observation mode, and thereafter holds the calculated correction value (step S17 of FIG. 10).

Note that, if the time period T during which the instruction signal is continuously outputted by continuous pushing down of the color balance switch 101 is shorter than the time period T3, the image processing apparatus control unit 42 invalidates all the correction values obtained by performing the processings from steps S13 to S17 of FIG. 10, and thereafter performs control to cause the color balance process unit 34 to hold the respective correction values in the three kinds of observation modes, originally held by the color balance process unit 34 (steps S16 and S11 of FIG. 10).

Also, if the time period T during which the instruction signal is continuously outputted by continuous pushing down of the color balance switch 101 is greater than the time period T3, the image processing apparatus control unit 42 validates the correction values newly obtained in the above-mentioned processings from steps S13 to S17 of FIG. 10. Thereafter, the image processing apparatus control unit 42 outputs, to the image signal output unit 35, a control signal having a content to cause the monitor 4 to display a character string indicating completion of white balance adjustments in all the three kinds of observation modes. Based on the control signal outputted from the image processing apparatus control unit 42, the image signal output unit 35 generates a character string indicating completion of white balance adjustments in all the three kinds of observation modes, which is displayed on the monitor 4 (step S18 of FIG. 10). The image processing apparatus control unit 42 performs control to cause the color balance process unit 34 to hold the respective correction values in the three kinds of observation modes, newly obtained in the processings from steps S13 to S17 of FIG. 10. Based on the control performed by the image processing apparatus control unit 42, the color balance process unit 34 holds the correction values newly obtained in the processings from steps S13 to S17 of FIG. 10, as respective correction values in the three kinds of observation modes (step S19 of FIG. 10).

Note that, in the case that the above-mentioned white balance adjustments supporting the plurality of observation modes are performed as the procedure shown in FIG. 10, if, for example, the endoscope apparatus 1 is set as one of the narrow band observation mode and the infrared observation mode, the image processing apparatus control unit 42 of the image processing apparatus 5 may perform control to invalidate the instruction signal outputted from the color balance switch 101. This makes it possible that, when performing white balance adjustments respectively supporting the three kinds of observation modes and the fluorescent light observation mode, using endoscope color-balance-adjustment tools each different for each observation mode, the user can perform the white balance adjustments supporting the observation modes without being confused with the endoscope color-balance-adjustment tools.

With the afore-mentioned processings being performed by the image processing apparatus 5, the user can prevent the endoscope apparatus 1, which includes the function to allow observation in, for example, the three kinds of observation modes, i.e., the normal observation mode, the infrared observation mode, and the narrow band observation mode, from being in a state where white balance adjustment is performed only in any one mode or where white balance adjustment is performed in each of the observation modes except any one mode. Moreover, in the above-mentioned processings, the image processing apparatus 5 performs control to cause the monitor 4 to display a character string indicating completion of white balance adjustments in all of the three kinds of observation modes. Thus, the user can perform observation in each of the three kinds of observation modes, having ensured that white balance adjustments have been performed in all of the three kinds of observation modes.

In addition, in the case of performing color balance adjustments respectively supporting the observation modes, using a correction value read from the storage unit 15 of the endoscope 2, the image processing apparatus 5 may perform the processings described below.

In the initial action after activation, the image processing apparatus control unit 42 of the image processing apparatus 5 starts reading a correction value associated to the connected light source apparatus 3, from the storage unit 15 of the endoscope 2 (step S21 of FIG. 11). The image processing apparatus control unit 42, on having read the correction value (step S22 of FIG. 11), judges whether or not data of the correction value has been normally read. In this state, the image processing apparatus control unit 42 also reads pieces of type information of the endoscope 2 and the light source apparatus 3 written in the storage unit 15 of the endoscope 2 and the storage unit 27 of the light source apparatus 3, respectively, and detects what kind of observation modes the endoscope 2 and the light source apparatus 3 support.

On judging that the data of the correction value has all been normally read (step S23 of FIG. 11), the image processing apparatus control unit 42 calculates, in each of the observation modes supported by the endoscope 2 and the light source apparatus 3, a correction value to be used in the each color balance adjustment based on the data of the read correction value (step S24 of FIG. 11), thereafter performing control to cause the color balance process unit 34 to hold the calculated correction value. The image processing apparatus control unit 42 then outputs, to the image signal output unit 35, a control signal to cause the monitor 4 to display a character string indicating completion of color balance adjustments in all of the observation modes supported by the endoscope 2 and the light source apparatus 3. Based on the control signal outputted from the image processing apparatus control unit 42, the image signal output unit 35 generates a character string indicating completion of color balance adjustment in each of the observation modes supported by the endoscope 2 and the light source apparatus 3, and displays the generated character string on the monitor 4 (step S25 of FIG. 11).

Note that the method to indicate the completion of color balance adjustments in all of the observation modes supported by the endoscope 2 and the light source apparatus 3 is not limited to the afore-mentioned. For example, the image processing apparatus control unit 42 may perform a control to turn the LED of the color balance setting incompletion display portion 102 of the operation panel 41 into a non-lighting state, and the LED of the color balance setting completion display portion 103 into a lighting state, to indicate the completion of color balance adjustments in all of the observation modes supported by the endoscope 2 and the light source apparatus 3.

Also, the image processing apparatus control unit 42, if judges that at least a part of the data of the correction value could not be normally read (step S23 of FIG. 11), specifies an observation mode supporting the data of the correction value that could be normally read, and an observation mode supporting the data of the correction value that could not be normally read. The image processing apparatus control unit 42 then calculates a correction value to be used in color balance adjustment only for the observation mode supporting the data of the correction value that could be normally read among the data of the correction values (step S26 of FIG. 11). The image processing apparatus control unit 42 then performs control to cause the color balance process unit 34 to hold the calculated correction value. Thereafter, the image processing apparatus control unit 42 outputs, to the image signal output unit 35, a control signal including a content to cause the monitor 4 to display a character string indicating incompletion of color balance adjustment in each of the observation modes supported by the endoscope 2 and the light source apparatus 3, and a content to prevent the monitor 4 from displaying a subject image picked up by the endoscope 2 in an observation mode in which the color balance adjustment is incomplete. Based on the control signal outputted from the image processing apparatus control unit 42, the image signal output unit 35 generates a character string reading, for example, "Please set color balance." as shown in FIG. 12, as a character string to indicate incompletion of white balance adjustment in the observation modes supported by the endoscope 2 and the light source apparatus 3, and displays the generated character string on the monitor 4 (step S27 of FIG. 11).

Note that the method to indicate the incompletion of color balance adjustment in the observation modes supported by the endoscope 2 and the light source apparatus 3 is not limited to the afore-mentioned. For example, the image processing apparatus control unit 42 may perform a control to turn the LED of the color balance setting incompletion display portion 102 of the operation panel 41 into a lighting state, and the LED of the color balance setting completion display portion 103 into a non-lighting state, to indicate the incompletion of color balance adjustment in each of the observation modes supported by the endoscope 2 and the light source apparatus 3.

The image signal output unit 35 further displays, based on the control signal outputted from the image processing apparatus control unit 42, another image such as, for example, a monochromatic image and a color bar image in, for example, an image display portion 302 as an area on the monitor 4 in which the image of the subject image picked up by the endoscope 2 is displayed, as shown in FIG. 12 (step S28 of FIG. 11).

Incidentally, in the observation using the endoscope apparatus 1, the user, for example, inputs a standard image as shown in FIG. 15 to a recording apparatus such as a VTR and printer both not shown, and displays a high-definition image as shown in FIG. 16 on the monitor 4. On a recording screen by the standard image, character strings or the like about the state of the endoscope apparatus 1 are displayed in notice display portions 601, 602 in such a manner to cover parts of the image display portion 603. On an observation screen by the high-definition image, character strings or the like about the state of the endoscope apparatus 1 are displayed in notice display portions 601*a*, 602*a* in such as manner to cover parts on an image display portion 603*a* which are generally the same as with the above-mentioned standard image. This allows the user to record the screen of the standard image, recognizing that the image display portion 603 on the record screen of the standard image and the image display portion 603*a* on the observation screen of the high-definition image are covered by the above-mentioned character strings or the like in generally the same manner.

Note that the character strings or the like displayed in the notice display portions 601, 602, 601*a* and 602*a* have a content to caution the user about, for example, malfunction of the light source apparatus 3. Therefore, after being displayed on the monitor 4, the character strings or the like displayed in the notice display portions 601, 602, 601*a* and 602*a* may be deleted after passage of a predetermined time period.

With the above-mentioned processings being performed in the image processing apparatus 5, the user can clearly distinguish, among observation modes supported by the endoscope 2 and the light source apparatus 3, between those subjected and not subjected to color balance adjustment to be performed in each observation mode.

In addition, with the above-mentioned processings being performed in the image processing apparatus 5, the user is prevented from viewing a subject image with a color tone different from a desired color tone, thus allowing the user, for example, to proceed with observing the inside of the living body in a state of decreased chance of mistaking a lesion region for a normal region than in conventional cases.

Note that the present invention is not limited to the above-mentioned embodiment, and may of course be subject to various changes and applications without departing from the spirit of the invention.

This application is filed claiming priority from Japanese Patent Application No. 2005-149886 applied in Japan on May 23, 2005, the disclosed contents of which being incorporated in this specification, claims, and drawings.

The invention claimed is:

1. An image processing apparatus comprising:
   a color balance adjustment tool including:
      a fluorescent light generating portion for emitting fluorescent light when radiated with excitation light; and
      an intensity variation correction value display portion for displaying an intensity variation correction value for correcting variation in intensity of fluorescent light emitted from the fluorescent light generating portion;
   an image signal input unit for inputting an image signal that includes:
      a fluorescent light image picked up by an image pickup unit when the excitation light is radiated to the color balance adjustment tool, and
      a reflection light image picked up by the image pickup unit when a light in a wavelength band different from that of the excitation light is radiated to the color balance adjustment tool;
   a control unit for calculating a coefficient value for changing a brightness value of the image signal based on the intensity variation correction value, a brightness value of the fluorescent light image, and a brightness value of the reflection light image; and
   a color balance process unit for performing color balance adjustment by changing the brightness value of the image signal using the coefficient value, wherein the control unit calculates the coefficient value using the mathematical expression:

$$WBKR = WBAF/(WBR \times WBCAF)$$

with WBKR being the coefficient value, WBAF being the brightness value of the fluorescent light image, WBR being the brightness value of the reflection light image, and WBCAF being the intensity variation correction value.

2. The image processing apparatus according to claim 1, wherein the color balance adjustment tool further includes a tubular body having an aperture portion with a diameter to allow insertion of a distal end portion of an endoscope that includes the image pickup unit.

3. The image processing apparatus according to claim 2 wherein the fluorescent light generating portion is provided on at least a part of an inner circumferential surface of the tubular body.

4. The image processing apparatus according to claim 1, further comprising a display apparatus, wherein the control unit performs control to cause the display apparatus to display an intensity variation correction value input screen including an intensity variation correction value input portion for inputting the intensity variation correction value.

5. The image processing apparatus according to claim 4, wherein the intensity variation correction value input screen is a screen that is displayed including:
   an operation guiding portion for showing a list of operations executable on the intensity variation correction value input screen, and
   a message to urge a user to prepare necessary operations in inputting the intensity variation correction value into the intensity variation correction value input portion.

6. An endoscope apparatus comprising:
   a color balance adjusting tool including:
      a fluorescent light generating portion for emitting fluorescent light when radiated with excitation light; and
      an intensity variation correction value display portion for displaying an intensity variation correction value for correcting variation in intensity of fluorescent light emitted from the fluorescent light generating portion;
   an endoscope including an image pickup unit for:
      picking up a fluorescent light image when the excitation light is radiated to the color balance adjustment tool,
      picking up a reflection light image generated when a light in a wavelength band different from that of the excitation light is radiated to the color balance adjustment tool, and
      outputting the picked-up fluorescent light image and the picked-up reflection light image as an image signal; and
   an image processing apparatus for:
      calculating a coefficient value for changing a brightness value of the image signal based on a brightness value of the fluorescent light image, a brightness value of the reflection light image, and the intensity variation correction value, and
      performing color balance adjustment by changing the brightness value of the image signal using the coefficient value,
   wherein the image processing apparatus calculates the coefficient value using the mathematical expression:

$$WBKR = WBAF/(WBR \times WBCAF)$$

with WBKR being the coefficient value, WBAF being the brightness value of the fluorescent light image, WBR being the brightness value of the reflection light image, and WBCAF being the intensity variation correction value.

7. The endoscope apparatus according to claim 6, wherein the color balance adjustment tool further includes a tubular body having an aperture portion with a diameter to allow insertion of a distal end portion of the endoscope that includes the image pickup unit.

8. The endoscope apparatus according to claim 7, wherein the fluorescent light generating portion is provided on at least a part of an inner circumferential surface of the tubular body.

9. The endoscope apparatus according to claim 6, further comprising a display apparatus, wherein the image processing apparatus performs control to cause the display apparatus to display an intensity variation correction value input screen including an intensity variation correction value input portion for inputting the intensity variation correction value.

10. The endoscope apparatus according to claim 9, wherein the intensity variation correction value input screen is a screen that is displayed including
   an operation guiding portion for showing a list of operations executable on the intensity variation correction value input screen, and
   a message to urge a user to prepare necessary operations in inputting the intensity variation correction value into the intensity variation correction value input portion.

11. A color balance adjusting method comprising:
   an image signal input step for inputting an image signal that includes:
      a fluorescent light subject image picked up by an image pickup unit when an excitation light is radiated to, the subject image including at least an image of a color balance adjustment tool that includes a fluorescent light generating portion and an intensity variation correction value display portion for displaying an intensity variation correction value for correcting variation in intensity of fluorescent light emitted from the fluorescent light generating portion; and
      a reflection light image picked up by the image pickup unit when a light in a wavelength band different from that of the excitation light is radiated to the color balance adjustment tool;
   an intensity variation correction value input judgment step for judging whether or not the intensity variation correction value has been input;
   a brightness value calculation step for calculating, based on the image signal, a mean value of brightness values in an image including one wavelength band of the fluorescent light image and a mean value of brightness values of the reflection light image, when it is judged that the intensity variation correction value has been inputted in the intensity variation correction value input judgment step;
   a coefficient value calculation step for calculating a coefficient value to be used for color balance adjustment of the image signal, based on the intensity variation correction value and each of the mean values calculated in the brightness value calculation step; and
   a color balance adjustment step for changing the brightness value of the image signal using the coefficient value,
   wherein in the coefficient value calculation step, the coefficient value is calculated using the mathematical expression:

$$WBKR = WBAF/(WBR \times WBCAF)$$

with WBKR being the coefficient value, WBAF being the brightness value of the fluorescent light image, WBR being the brightness value of the reflection light image, and WBCAF being the intensity variation correction value.

12. The color balance adjusting method according to claim 11, further comprising:
- an insertion step of inserting a distal end portion of an endoscope that includes the image pickup unit through an aperture portion of a tubular body of the color balance adjustment tool into the tubular body; and
- an excitation light radiation step of radiating excitation light to the fluorescent light generating portion that is provided on at least a part of an inner circumferential surface of the tubular body.

* * * * *